(12) United States Patent
Rebe (10) Patent No.: US 8,753,835 B2
(45) Date of Patent: Jun. 17, 2014

(54) COMPRESSED GAS MICROBIAL TEST UNIT

(71) Applicant: Parker-Hannifin Corporation, Cleveland, OH (US)

(72) Inventor: Paul Eric Rebe, Bow, NH (US)

(73) Assignee: Parker-Hannifin Corporation, Cleveland, OH (US)

( * ) Notice: Subject to any disclaimer, the term of this patent is extended or adjusted under 35 U.S.C. 154(b) by 13 days.

(21) Appl. No.: 13/630,106

(22) Filed: Sep. 28, 2012

(65) Prior Publication Data
US 2013/0084597 A1 Apr. 4, 2013

Related U.S. Application Data

(60) Provisional application No. 61/542,350, filed on Oct. 3, 2011.

(51) Int. Cl.
*C12Q 1/04* (2006.01)
(52) U.S. Cl.
USPC .......................................... 435/34; 435/288
(58) Field of Classification Search
USPC ........................................................ 435/36
See application file for complete search history.

(56) References Cited

U.S. PATENT DOCUMENTS

2006/0257287 A1* 11/2006 Call et al. ..................... 422/83
2011/0167931 A1 7/2011 Vellutato, Jr. ............. 73/863.11

OTHER PUBLICATIONS

Juozaitis et al., Applied Environmental Microbiology, vol. 60, No. 3, p. 861-870, 1994.*
Terzieva et al., Applied and Environmental Microbiology, vol. 62, No. 7, p. 2264-2272, 1996.*
Lawrence et al., Bacillus anthracis Spores (Etiologic Agent of Anthrax) in Air, The National Occupational Research Agenda, p. 81-106, Salt Lake City, Utah: The University of Utah, 2003.*
Dotson et al. (Proceedings: Indoor Air, 2002).*
Zefon (Air-O-Cell brochure, http://www.zefon.com/store/air-o-cell-sampling-cassette.html, accessed Jan. 10, 2014).*
Grinsphun et al. (Journal of Environmental Monitoring, vol. 9, p. 855-861, 2007).*
International PBI S.p.A.; "Compressed Air/Gas Microbial Testing for Sterility Control in Clean Room According to ISO 8573-7"; Mar. 2009.
Biocompare; "Testing Compressed Air Lines for Microbiological Contamination"; May 2006.
PMV Air Samplers; "RCG Comp Gas/Confined Space Sampler"; 2009.

* cited by examiner

*Primary Examiner* — Susan Hanley
*Assistant Examiner* — Damon Bowe
(74) *Attorney, Agent, or Firm* — Renner, Otto, Boisselle & Sklar, LLP (57) ABSTRACT

Provided is a microbial test unit for detecting microbes in a compressed gas. The microbial test unit includes a decompression region and a sampling region in fluid communication with the decompression region and separated from the decompression region by a plate. The decompression region and the sampling region define a flow path. An inlet communicates with the decompression region such that compressed gas entering the decompressing region is incident on the plate for effectuating decompression of the gas prior to the gas passing into the sampling region. The microbial test unit may be used in conjunction with a growth medium substrate to form a microbial test system. The microbial test unit provides the ability to test compressed gas directly input to the unit due to positive pressure from the compressed gas pushing the microbes onto the microbial growth substrate.

15 Claims, 8 Drawing Sheets

COMPRESSED GAS MICROBIAL TEST UNIT

RELATED APPLICATIONS

This application claims the benefit of U.S. Provisional Application No. 61/542,350 filed Oct. 3, 2011, the disclosure of which is incorporated herein by reference in its entirety.

FIELD OF INVENTION

The present invention relates generally to microbial detection, and more particularly to an apparatus and method for detecting microbes in a compressed gas.

BACKGROUND

Compressed gas is used in a number of applications in the food industry. For example, compressed air is used as an ingredient in whipped products such as ice cream and yogurt. Compressed air is also used as a processing tool to slice or cut soft food products and to open packages before filling with food product.

Food manufacturers are under pressure to validate the safety of all ingredients and processes for regulatory compliance. But there is currently no standard method to evaluate the microbial content of compressed gas used in the food industry.

SUMMARY OF INVENTION

The present invention provides a microbial test unit for detecting microbes in a compressed gas. The microbial test unit includes a decompression region and a sampling region in fluid communication with the decompression region and separated from the decompression region by a plate. The decompression region and the sampling region define a flow path. An inlet communicates with the decompression region such that compressed gas entering the decompressing region is incident on the plate for effectuating decompression of the gas prior to the gas passing into the sampling region. The microbial test unit may be used in conjunction with a growth medium substrate to form a microbial test system. The microbial test unit provides the ability to test compressed gas directly input to the unit due to positive pressure from the compressed gas pushing the microbes onto the microbial growth substrate.

According to one aspect of the invention, a compressed gas microbial test unit is provided that includes a housing extending along a longitudinal axis between a first end and a second end, the housing defining an internal cavity comprising a decompression region for decompressing compressed gas input to the internal cavity and a sampling region in fluid communication with the decompression region for containing a growth medium substrate, the decompression region and the sampling region defining a flow path through the internal cavity. A plate is disposed in the internal cavity and separates the decompression region and the sampling region. An inlet is at a first end of the housing proximate the decompression region and an outlet is at a second end of the housing proximate the sampling region, the inlet communicating with the decompression region such that compressed gas entering the decompressing region from the inlet is incident on the plate for effectuating decompression of the gas prior to the gas passing into the sampling region.

In

In yet another embodiment, the growth medium substrate comprises an agar growth medium.

According to yet another aspect of the invention, a method for testing a microbial content of a compressed gas includes inputting compressed gas into an internal cavity of a housing, decompressing the compressed gas in a decompression region of the internal cavity, introducing the decompressed gas into a sampling region of the internal cavity, and bringing the decompressed gas into contact with a growth medium substrate contained in the sampling region.

In an embodiment, the compressed gas is input to the internal cavity at a flow rate equal to or greater than about 5 CFM.

In another embodiment, the decompression region and the sampling region are separated by a plate disposed in the internal cavity, and the decompressing comprises directing the input compressed gas against the plate for effectuating decompression of the gas. The decompressed gas is introduced into the sampling region by passing through a gap formed between the housing and the plate.

In yet another embodiment, the sampled gas is passed through one or more radially extending passages proximate the second end of the housing, and the sampled gas is output from the outlet.

The foregoing and other features of the invention are hereinafter described in greater detail with reference to the accompanying drawings.

DETAILED DESCRIPTION

The principles of the present application have particular application to detecting microbes in a compressed gas (e.g., compressed air) used in the food manufacturing industry, and thus will be described below chiefly in this context. It will of course be appreciated, and also understood, that the principles of the invention may be useful for other gasses (e.g., nitrogen, oxygen, carbon dioxide, etc.) and/or in other applications (e.g., cosmetics, beverages, biotech applications, etc.) where microbial detection is desired.

Figure 1:
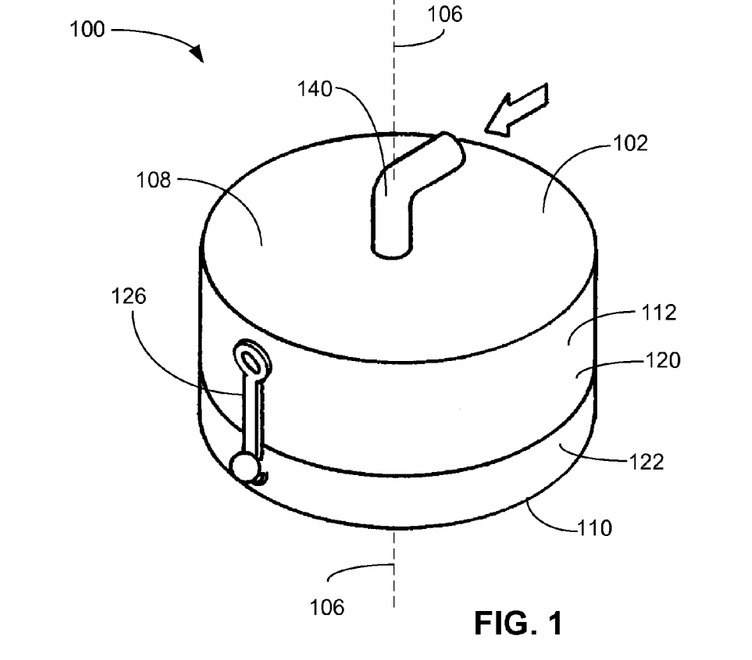
FIG. 1 is a perspective view of an exemplary microbial test unit shown in a closed state.
Figure 2:
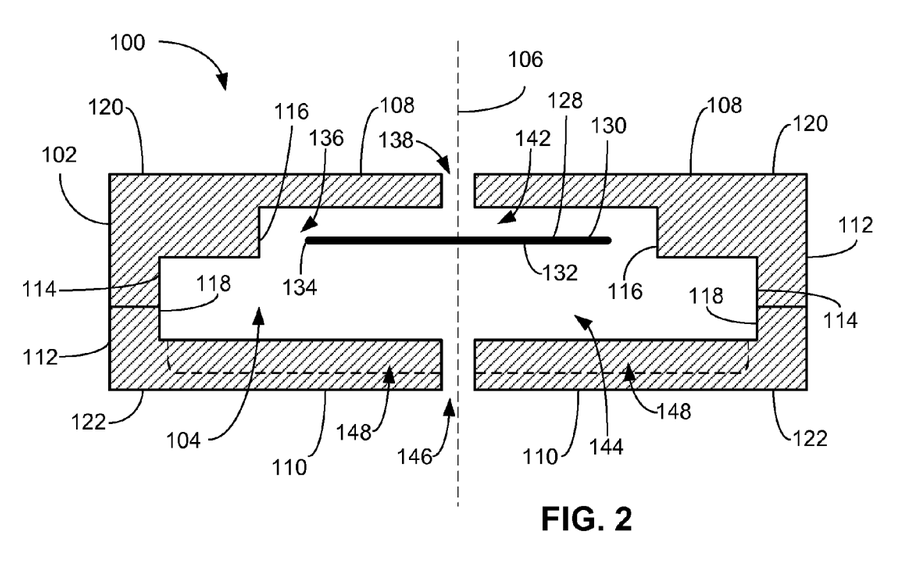
FIG. 2 is a schematic cross-sectional view of the exemplary microbial test unit shown in FIG. 1.

Referring now in detail to the drawings and initially to FIGS. 1 and 2, a microbial test unit is illustrated generally at 100. The microbial test unit 100 includes a housing 102. The housing 102 is configured as a hollow body surrounding an internal cavity 104. The housing 102 defines a longitudinal axis 106 extending between a first end 108 and a second end 110. The housing includes an outer surface 112 and an inner surface 114 opposite the outer surface 112. The outer surface 112 extends along the longitudinal axis 106 between the first end 108 and the second end 110 of the housing 102. The inner surface 114 extends along at least a portion of the longitudinal axis 106, the periphery thereof defining the shape of the internal cavity 104. In the example shown, the periphery of the inner surface 114 extending along the longitudinal axis 106 is generally cylindrical in shape. In other embodiments, the periphery of the inner surface may be another suitable shape such as a rectangular prism or polygonal prism.

In some embodiments, the inner surface 114 of the housing 102 is a stepped surface extending along the longitudinal axis 106. In the example shown in FIG. 2, the stepped inner surface 114 includes a first stepped portion 116 proximate the first end of the housing 102 and a second stepped portion 118 proximate the second end of the housing 102. The periphery of the second stepped portion 118 is larger than the periphery of the first stepped portion 116. In one embodiment, the periphery of the first stepped portion 116 may be generally cylindrical in shape and may have a diameter from about 2.0 inches to about 3.0 inches. In another embodiment, the periphery of the first stepped portion 116 may be generally cylindrical in shape and may have a diameter of about 2.5 inches. In one embodiment, the periphery of the second stepped portion 118 may be generally cylindrical in shape and may have a diameter from about 3.75 inches to about 4.75 inches. In another embodiment, the periphery of the second stepped portion 118 may be generally cylindrical in shape and may have a diameter of about 4 inches. The periphery of the first stepped portion 116 and the periphery of the second stepped portion 118 may be any suitable size.

Figure 3:
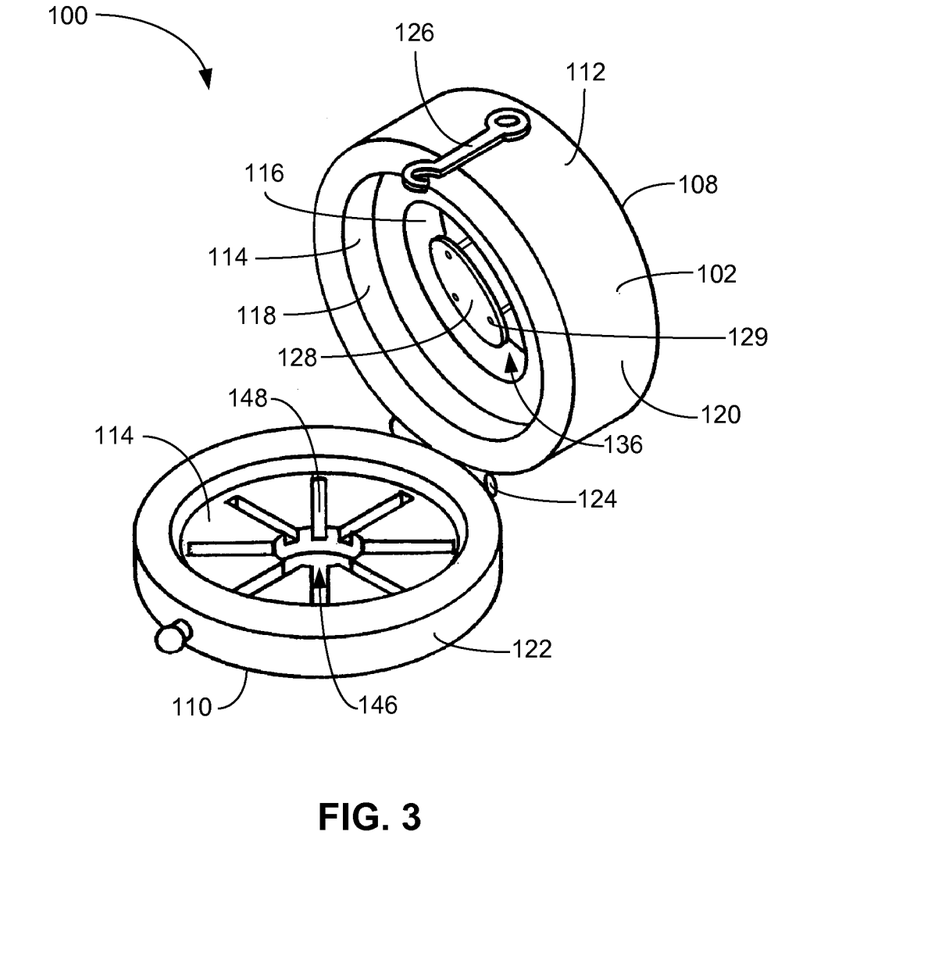
FIG. 3 is a perspective view of the exemplary microbial test unit of FIG. 1 shown in an open state.

The housing may include a first portion 120 and a second portion 122 removably attached to the first portion 120. FIGS. 1 and 2 show an exemplary microbial test unit in a closed position. In the closed position, the first portion 120 and the second portion 122 of the housing 102 collectively form the inner cavity 104. FIG. 3 shows the exemplary microbial test unit 100 in an open position. In the example shown, the microbial test unit includes a hinge 124 attached to the first portion 120 and the second portion 122 for effectuating opening and closing of the housing 102, and a locking mechanism 126 for retaining the first portion 120 and the second portion 122 in the closed position. In other embodiments, the microbial test unit 100 instead includes a plurality of locking mechanisms 126 disposed about the outer periphery of the housing 102 for retaining the first portion 120 and the second portion 122 in the closed position.

A plate 128 is disposed in the internal cavity 104. The plate 128 includes opposed surfaces 130, 132 and at least one edge surface 134 extending between the opposed surfaces 130, 132. At least one of the surfaces 130, 132 of the plate 128 may be nominally perpendicular to the longitudinal axis 106. Although in other embodiments, at least one of the major surfaces 130, 132 of the plate may be arranged at another suitable angle relative to the longitudinal axis 106. The major surface 130 of the plate 128 is spaced apart from the inner surface 114 of the housing 102 proximate the first end 108. In some embodiments where the inner surface 114 of the housing 102 is a stepped surface, the spacing does not extend beyond the first stepped portion 120. The plate may be attached to the housing, for example, by mechanically fastening the plate to the first portion of the housing via a plurality of fasteners 129 (e.g., as shown in FIG. 3).

The at least one edge surface 134 defines the outer periphery of the plate 128. In the embodiment shown, the edge surface 134 defines a cylindrical periphery. In other embodiments, the edge surface 134 defines another suitable shape such as a rectangular or polygonal shape. The periphery of the plate 128 may have a shape similar to or different from the periphery of the inner surface 114 of the housing 102. A gap 136 is present between the at least one edge surface of the plate and the inner surface (e.g., the first stepped surface 116) of the housing 102. In the example shown, the gap is an annular gap. In other embodiments, the size and shape of the gap may depend on the size and shape of the outer periphery of the plate, and the size and shape of the periphery of the inner surface 114. In one embodiment, the gap may be an annular gap and the distance between the inner surface 114 and the edge surface 134 of the plate that defines the gap may be from about 0.25 inch to about 0.75 inch.

The housing 102 includes an inlet 138 at the first end 108. As shown in FIG. 1, the inlet may include a connector 140 for connecting the microbial test unit 100 to a compressed gas source. Any suitable connector may be used, such as a quick-connect or threaded connector. The flow rate of the compressed gas into the microbial test unit 100 is defined at least in part by the size of the inlet. The size of the inlet may be any suitable size, e.g., to provide a suitable compressed gas flow rate. In one embodiment, the size of the inlet may range from about 0.25 inch to about 1 inch. In another embodiment, the size of the inlet may range from about 0.5 inch to about 0.75 inch. In yet another embodiment, the size of the inlet may be about 0.7 inch.

The internal cavity 104 includes a decompression region 142 proximate the inlet 140 at the first end 108 of the housing 102. The decompression region 142 of the internal cavity 104 is at least partially defined by a portion of the inner surface 114 (e.g., by the first stepped portion 116) and by the surface 130 of the plate 128. The inlet 138 communicates with the decompression region 142 such that compressed gas entering the decompressing region from the inlet 138 is incident on the surface 130 of the plate 128. As described in more detail below, the plate 128 is configured to direct the compressed gas incident on the plate 128 radially outward with respect to the longitudinal axis 106, thereby effectuating decompression of the compressed gas.

The internal cavity 114 additionally includes a sampling region 144 proximate the second end 110 of the housing 102. The sampling region 144 is separated from the decompression region 142 by the plate 128, and is at least partially defined by a portion of the inner surface 114 (e.g., the second stepped portion 118) and by the surface 132 of the plate 128. The sampling region 144 is suitable for containing a growth medium substrate for collecting microbes present in the gas. In some embodiments, separation of the first portion 120 and the second portion 122 of the housing 102 provides access to the sampling region 144 and any growth medium substrate disposed therein.

The gap 136 formed between the inner surface 114 and the edge surface 134 of the plate 128 provides for fluid communication between the decompression region 142 and the sampling region 144. The gap 138 forms a passageway through which decompressed gas may pass from the decompression region 142 into the sampling region 144.

The housing 102 includes an outlet 146 at the second end 110. In the example shown, the outlet 146 is a circular orifice. In other embodiments, the outlet may be any suitable size and shape. The orifice may output the gas from the housing 102 to the atmosphere. Although not specifically shown, in some embodiments the outlet may include a suitable connector (e.g., a quick-connect or threaded connector) for connecting to a receptacle to collect the gas passed through the microbial test unit 100.

The inner surface 114 of the housing 102 proximate the second end 110 is additionally defined by flow channels 148. The flow channels 148 extend radially with respect to the longitudinal axis 106 and terminate at the outlet 146. The inner surface 114 may include any suitable number of channels 148.

Figure 4:
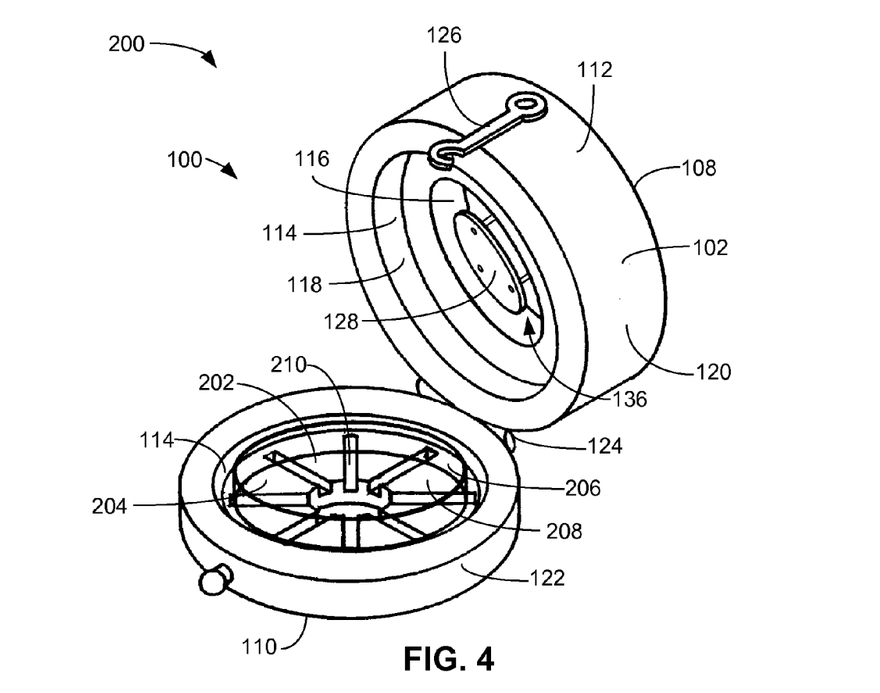
FIG. 4 is a perspective view of an exemplary microbial test system shown in an open state.
Figure 5:
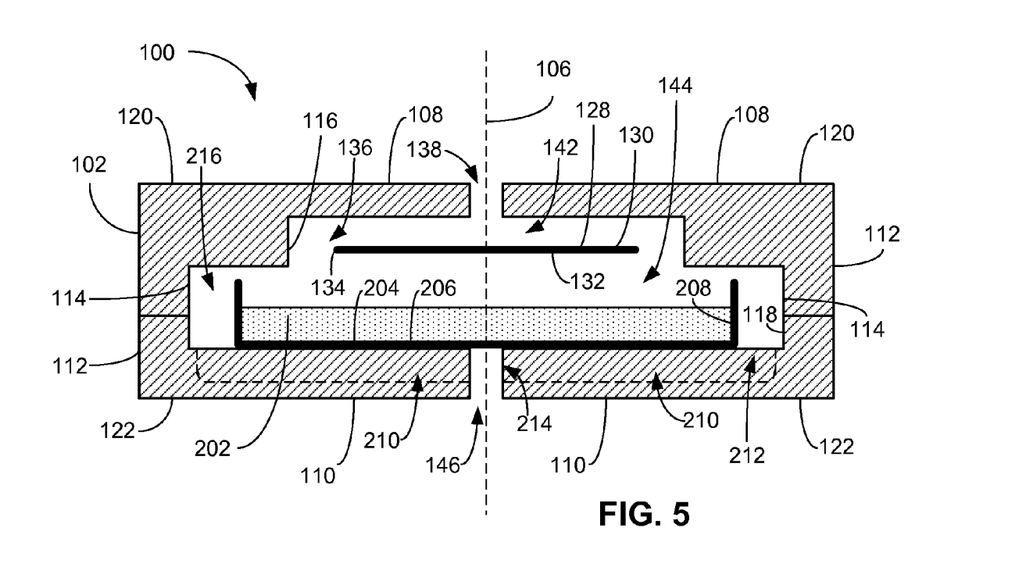
FIG. 5 is a schematic cross-sectional view of an exemplary microbial test system.

Referring now to FIGS. 4 and 5, a microbial test system is shown at 200. The microbial test system includes the microbial test unit 100. In addition, a growth medium substrate 202 is disposed in the sampling region 144 of the microbial test unit 100. The growth medium substrate 202 is positioned such that the decompressed gas passing through the gap 136 into the sampling region 144 is incident on the growth medium substrate. The growth medium substrate 202 may be any suitable substrate for collecting and culturing microbes. In one embodiment, the growth medium substrate is an agar substrate. The agar substrate may be mixed with any suitable nutrient media.

The growth medium substrate 202 may be retained in a receptacle 204 disposed in the sampling region 144. The receptacle 204 includes a base member 206 and a side member 208 extending from the base member 206. In an example, the receptacle may be a standard size Petri dish. In one example, the base member 206 has a diameter of about 3.5 inches and the side member 208 has a length of about 0.6 inch.

The base member 206 of the receptacle 204 closes off a portion of the radially extending channels 148 to form radially extending passages 210. The portion of each extending channel 148 that radially extends beyond the base member 206 constitutes a passage inlet 212. The portion of each channel terminating at the outlet constitutes a passage outlet 214. The passage inlet 212 is in fluid communication with the sampling region 144 by a gap 216 formed between the receptacle 204 and the inner surface 114 of the housing 102. The gap 216 effectuates passage of the sampled gas into the radially extending passages 210.

Figure 6:
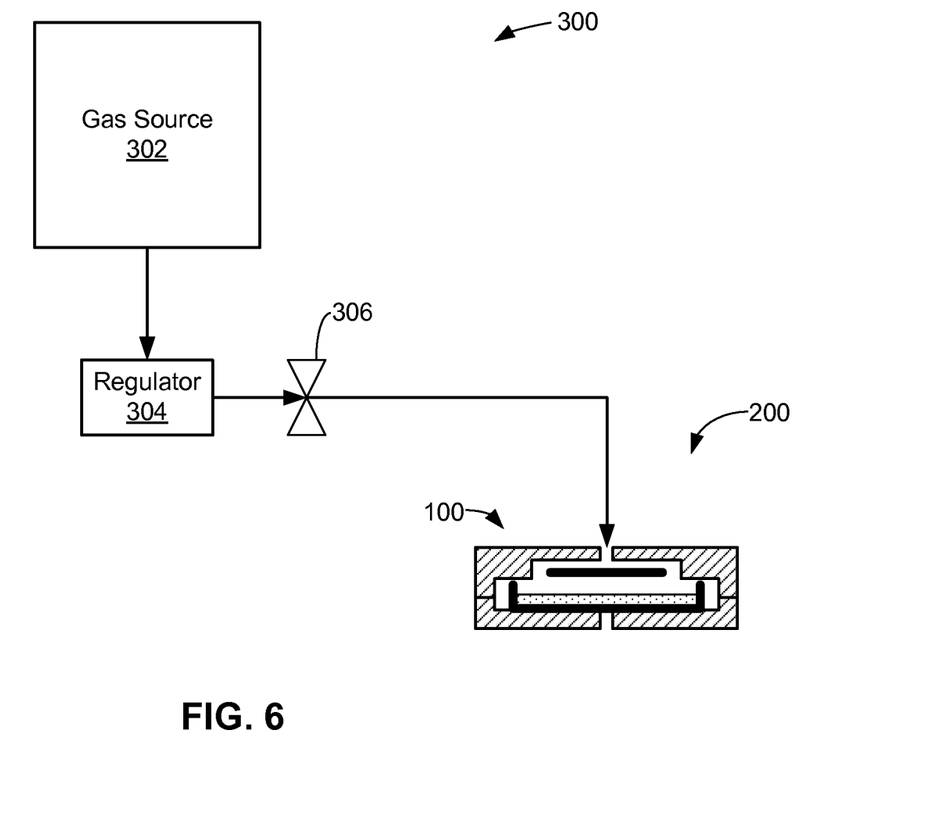
FIG. 6 is a schematic diagram showing an exemplary compressed gas system including an exemplary microbial test system.

Referring now to FIG. 6 a compressed gas system including the microbial test system 200 is shown at 300. A gas source 302 is in fluid communication with the inlet of the microbial test unit 100. In one embodiment, the gas source is compressed air suitable for use in the food manufacturing industry. In other embodiments, the gas may be another type of gas (e.g., nitrogen, oxygen, carbon dioxide, etc.) and/or may be suitable for use in another application (e.g., cosmetics, beverages, biotech applications, etc.) where microbial testing of the gas is desired.

The gas source is coupled to the microbial test unit through a regulator 304 and at least one valve 306. The at least one valve 306 controls the flow of compressed gas from the gas source 302 to the microbial test system 200. The regulator 304 is configured to regulate the pressure and flow rate of the compressed gas input to the microbial test system 200. In one embodiment, the pressure of the compressed gas input to the microbial test system 200 is from about 20 psi to about 80 psi. In another embodiment, the pressure of the compressed gas input to the microbial test system 200 is from about 40 psi to about 70 psi. In yet another embodiment, the pressure of the compressed gas input to the microbial test system 200 is equal to or greater than about 60 psi.

An orifice (not shown) is present at the outlet of the regulator that controls the flow rate of gas into the microbial test system 200. The orifice may be any suitable shape and size. In one embodiment, the orifice is an annular orifice having a diameter of about 0.050 inch to about 0.1 inch. In another embodiment, the orifice is an annular orifice having a diameter of about 0.060 inch to about 0.080 inch. In yet another embodiment, the orifice is about 0.070 inch. The flow rate of the compressed gas input to the microbial test system 200 is a function of the pressure of the compressed gas and the size of the orifice. For example, in an embodiment where the regulator 304 regulates the compressed gas to about 60 psi and the orifice has a diameter of about 0.070 inch, the flow rate of the compressed gas input to the microbial test system 200 may be about 5 CFM. In other embodiments, the pressure of the compressed gas and/or the size of the orifice may be set to provide a suitable flow rate of the compressed gas into the microbial test system 200. For example, in one embodiment, the pressure of the compressed gas and/or the size of the orifice may be set to provide a flow rate of the compressed gas input to the microbial test system 200 from about 0.5 CFM to about 10 CFM. In another embodiment, the pressure of the compressed gas and/or the size of the orifice may be set to provide a flow rate of the compressed gas input to the microbial test system 200 from about 4 CFM to about 8 CFM. In yet another embodiment, the pressure of the compressed gas and/or the size of the orifice may be set to provide a flow rate of the compressed gas input to the microbial test system 200 equal to or greater than about 5 CFM.

The decompression region 142 and the sampling region 144 define a flow path through the internal cavity 104 of the microbial test unit 100 between the inlet 138 and the outlet 146. In embodiments where the microbial test unit 100 and the growth medium substrate 202 (e.g., retained in the receptacle 204) form the microbial test system 200, the flow path may additionally include the radially extending passages 210 formed by the channels 148 and the base member 206 of the receptacle 204. The flow of gas through the microbial test system 200, as well as the process for testing a microbial content of a compressed gas will now be described with reference to FIGS. 7A-7E. As shown in the figures, the microbial test system 200 is provided as the microbial test unit 100 having the microbial growth substrate retained by the receptacle 204 and contained in the sampling region 144.

Figure 7A:
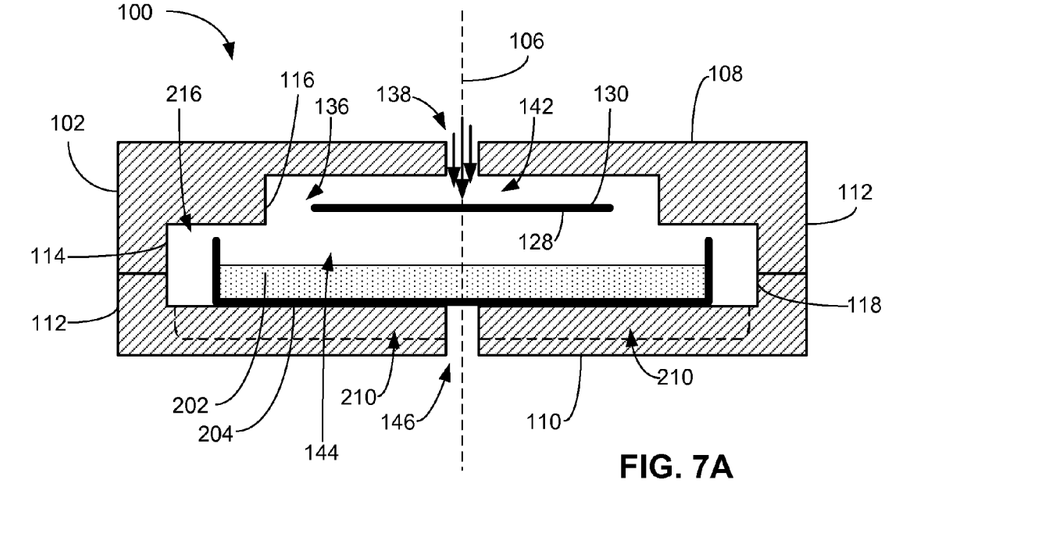
FIGS. 7A-7E are schematic cross-sectional views showing the flow of gas through an exemplary microbial test system.

As shown in FIG. 7A, compressed gas is input to the decompression region 142 of the internal cavity 104 through the inlet. The compressed gas is incident on the surface 130 of the plate 128.

Figure 7B:
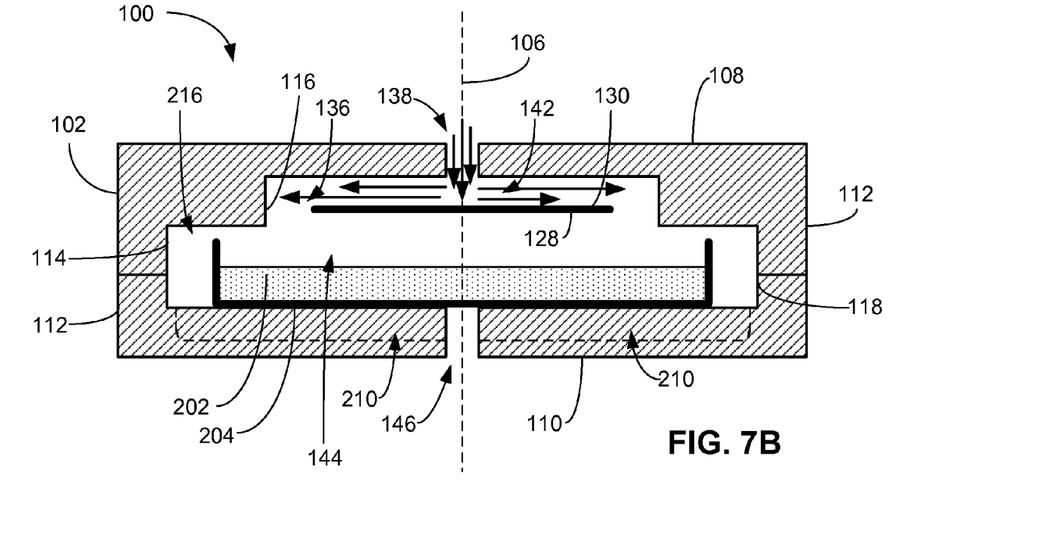

As shown in FIG. 7B, the compressed gas incident on the plate 128 is directed radially outward with respect to the longitudinal axis 106. This radial spreading effectuates decompression of the compressed gas. In some embodiments, the compressed gas may be decompressed to atmospheric or near atmospheric conditions. In order to sample compressed gas, it must initially be decompressed to atmospheric or near atmospheric conditions. Decompression of the gas reduces the impaction velocity and stress of the microbial cells onto the microbial growth substrate, thereby improving the microbial recovery.

Figure 7C:
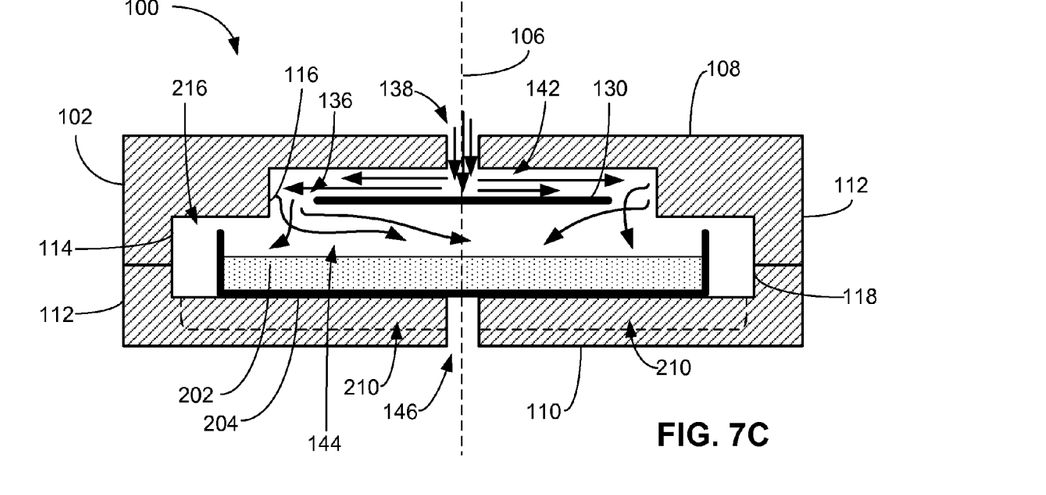

The decompressed gas is incident the first stepped portion 116 of the internal surface 114. As shown in FIG. 7C, the gas incident on the first stepped portion 116 is redirected through the gap 136 into the sampling region 144. The redirection of the gas and the size of the gap 136 through which the decompressed gas passes creates turbulent flow of the gas into the sampling region 144. The decompressed gas is therefore brought into contact with the growth medium substrate 202. The turbulent flow aids in the distribution of decompressed gas incident the microbial growth substrate 202.

Figure 7D:
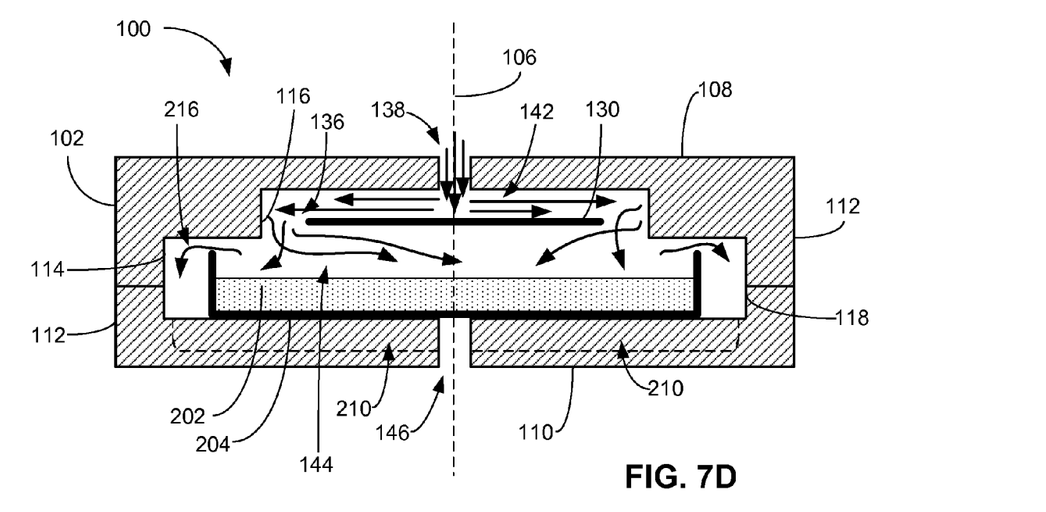
Figure 7E:
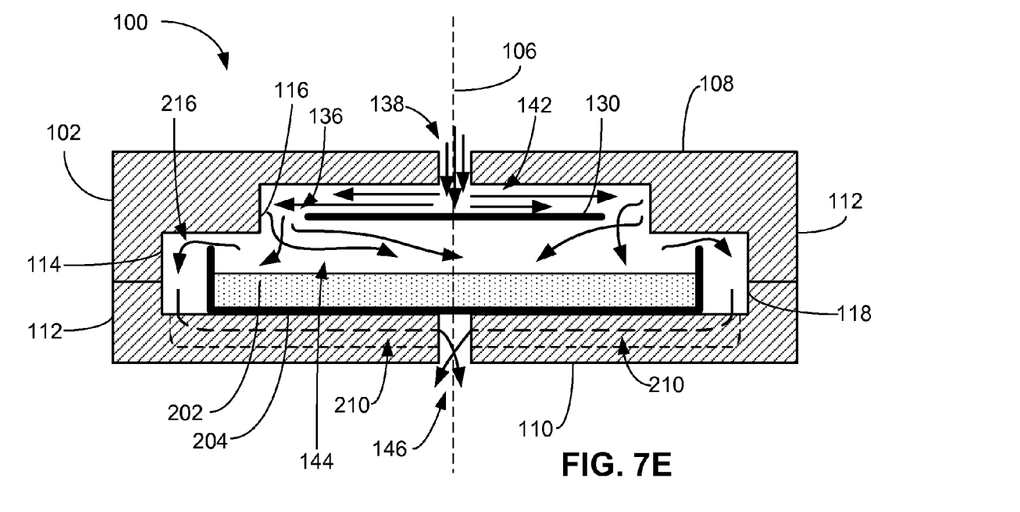

As shown in FIG. 7D, the sampled gas flows through the gap formed between the receptacle 204 and the inner surface 114 of the housing 102. As shown in FIG. 7E, the sampled gas enters the channel inlet 212, flows through the passage 210, and exits the passage outlet 214.

The testing process described in FIGS. 7A-7E may be conducted for any suitable amount of time. In one embodiment, the time of performing the testing process is from about 30 seconds to about 5 minutes. In another embodiment, the time of performing the testing process is from about 2 minutes to about 3 minutes. Following the testing process, the microbial growth substrate may be removed from the microbial test unit 100 and may be analyzed for the presence of microbes. For example, the microbial growth substrate may be incubated for a suitable time at a suitable temperature to facilitate growth of microbes collected on the microbial growth substrate. The microbial growth substrate may subsequently be analyzed for the presence of microbial growth.

The microbial test unit of the present disclosure provides the advantage of providing a test unit to which compressed gas may be directly input. The microbial test unit provides the ability to directly test compressed gas and collect bacteria due to positive pressure from the compressed gas pushing the microbes onto the microbial growth substrate. The microbial test unit is portable and does not require a power source. As such, the microbial test unit is particularly applicable as a field test unit, e.g., in a food processing plant environment. Since the microbial test unit can use a standard Petri dish for sampling, it can be used for performing different types of microbial isolation by, for example, using Rose Bengal-Streptomycin agar for selective collection of airborne yeast and molds.

By contrast, other commercially available air sampling units require the initial decompression of the compressed gas in a decompression chamber separate from the air sampling unit. The decompressed gas is then sampled by utilizing a pump to vacuum the air through the air sampling unit. These units are often large laboratory bench models, which limited their usefulness in the field (e.g., in a food processing plant environment).

The following example, demonstrates the compressed gas sampling capability of the microbial test system of the present disclosure as compared to a commercially-available Andersen single stage viable particle sizing sampler.

Figure 8:
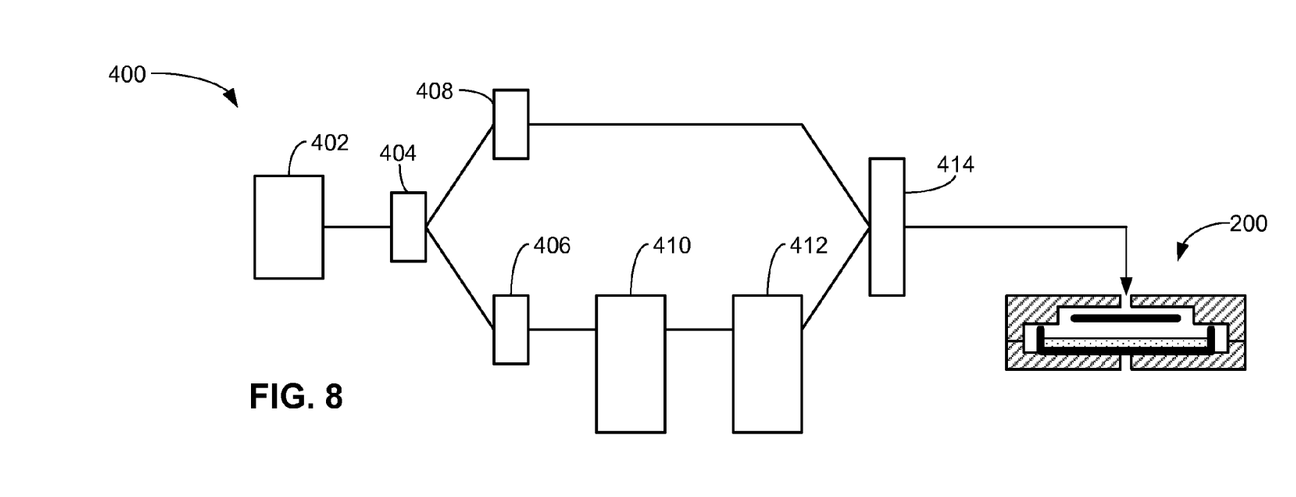
FIGS. 8 and 9 are schematic diagrams showing experimental bacterial nebulization and sampling systems.
Figure 9:
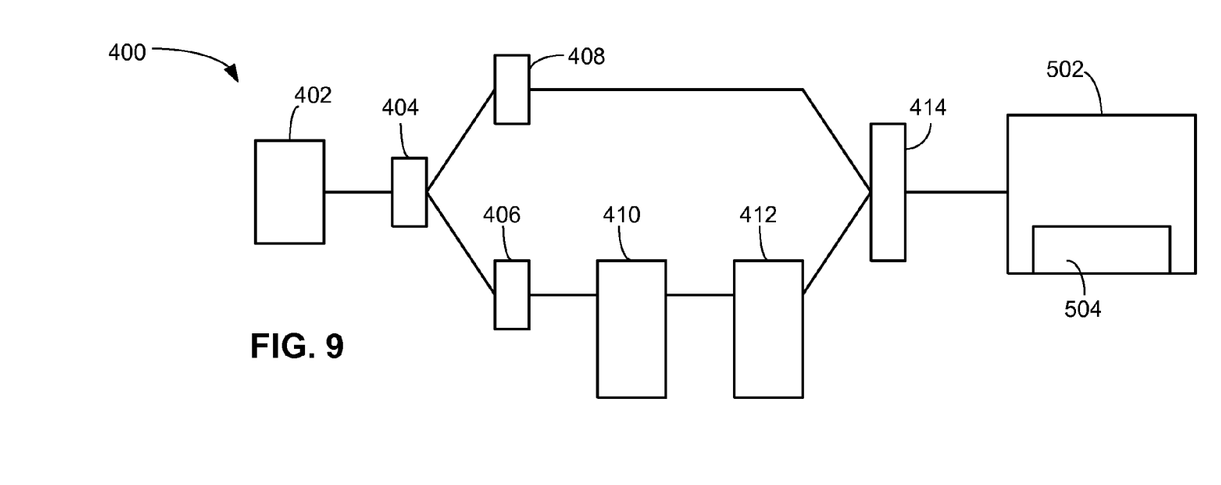

Referring now to FIG. 8, an experimental bacterial nebulization and sampling system including the microbial test system 200 is schematically shown at 400. The microbial test system 200 is coupled to the gas source 402 through regulators 404, 406, 408, nebulizer 410, desiccant 412, and flow rate meter 414.

The gas source 402 is compressed air suitable for use in the food manufacturing industry. The pressure and flow rate of the compressed air exiting the gas source is regulated by regulator 404. For purposes of the experiment, the pressure of the compressed air was regulated to 60 psi.

The regulators 406 and 408 are coupled in parallel to the regulator 404. A portion of the compressed air exiting the regulator 404 is passed through the regulator 406, and another portion of the compressed air exiting the regulator 406 is passed through the regulator 406. For purposes of the experiment, the pressure of the compressed air passed through the regulator 406 was further regulated to 45 psi, and the pressure of the compressed air passed through the regulator 408 was further regulated to 40 psi.

The nebulizer 410 is coupled to the regulator 406. The compressed air exiting the regulator 406 passes through the nebulizer (at 45 psi) to entrain bacteria in the compressed air. For purposes of the experiment, Gram positive, non-spore forming bacteria *Micrococcus luteus* ATCC 4698 was contained in the nebulizer. This organism is commonly used in testing the recovery of bacteria from aerosols. *Micrococcus luteus* ATCC 4698 has a round to slightly elongated round shape with a diameter between 0.5-1 µm. Cells of this organism after growing in broth can exist as single cells, groups of tetrads or clumps. Broth cultures for each experiment were prepared by inoculating a loopful of working culture into 50 ml tryptic soy broth (TSB) and grown with agitation (200 rpm) for 18 hours at 32° C.

The desiccant 412 is coupled to the nebulizer 410 for removing excess moisture in the system. The desiccant 412 used for purposes of the experiment was DRIERITE gypsum desiccant, available from W. A. Hammond Drierite Co, Xenia Ohio.

The flow rate meter 414 is coupled to the desiccant 412 and the regulator 408. The flow rate meter 414 monitors the flow of the compressed gas to the microbial test system 200. The compressed air exiting the desiccant 412 is rejoined with the compressed air exiting the regulator 408 at 40 psi. In the experimental bacterial nebulization and sampling system 400 shown in FIG. 8, the compressed air is input to the microbial test system 200 at 40 psi.

FIG. 9 shows an experimental bacterial nebulization and sampling system 500 similar to the experimental bacterial nebulization and sampling system 400 shown in FIG. 8. However, the experimental bacterial nebulization and sampling system 500 includes an air box in place of the microbial test system 200. As such, the compressed air exiting the flow rate meter 414 is input to the air box 502 from the flow rate meter 414. The air entering the air box 502 is decompressed to atmospheric pressure.

An Andersen One Stage viable particle sizing sampler 504 ("Andersen sampler") is disposed in the air box 502. The Andersen sampler 502 is a commercially-available impactor developed with the National Institute for Occupational Safety and Health (NIOSH) and is an approved method for bioaerosol sampling of non-compressed air by the Environmental Protection Agency (EPA), Occupational Safety and Health Association (OSHA) and the Food and Drug Administration (FDA). The Andersen sampler houses a Petri dish. The housing of the Andersen sampler has 400 holes with a cut off diameter of 0.65 μm and designed to sample aerosols of bacteria from air at atmospheric pressures using a vacuum pump to draw in air. Air drawn into the Andersen sampler is impacted against the Petri dish. For purposes of the experiment, the Andersen sampler is attached to a calibrated vacuum pump (not shown) which pulls air through the pin point holes onto the Petri dish at a rate of 0.9994 CF/min (28.3 L/min).

The experimental procedure proceeded as follows:

With continued reference to FIG. 8, a sterile agar plate was placed into the ethanol sanitized microbial test unit 100 so as to form the microbial test system 200. The compressed gas was input to the microbial test system 200 at a flow rate of 1.6 CFM. Each run was performed for a different amount of time (i.e., 20, 40, 80, and 160 seconds), and timing was started at the initiation of air into the nebulizer. After each sampling run, the agar plate was removed and the microbial test unit 100 was wiped down with a 70% ethanol solution and a new agar plate was added. In addition, before and after each sampling run, the nebulizer was weighed to calculate the approximate volume of liquid nebulized during the sampling run. After each sampling run, the used liquid was removed and replaced with a fresh bacterial solution for the next sampling run. A single microbial test unit 100 was used and each sampling time was performed in triplicate, with fresh bacterial solution in the nebulizer for each run.

With continued reference to FIG. 9, a sterile agar plate was placed into an ethanol sanitized Andersen sampler. For each test, the compressed air was turned on and the system (air, nebulizer) was run for 1 min with a measured flow rate on 1.8 L/min, after which the vacuum pumps attached to the Andersen sampler would be manually started, and then turned off at the desired time using a timed switch after 32, 64, 128, or 256 seconds. The Andersen sampler was used at a flow rate of 0.9994 CFM. Accordingly, the sampling times for the Andersen sampler were adjusted to obtain similar volumes of air on to those sampled with the microbial test system 200. The air pressure and flow rates were recorded for each run. After each sampling run, the agar plate was removed from the Andersen sampler, the Andersen sampler and sample box were wiped down with 70% ethanol, and a fresh agar plate was added. Before and after each sampling run, the nebulizer was weighed to calculate the approximate volume of liquid nebulized in each run. After each run, the used liquid was removed and replaced with a fresh bacterial solution for the next sampling run.

The agar plates used in the sampling runs were incubated at 32° C. for 24 hours. Following the incubation period, colony numbers were determined using an automated plate counting system (Q-count, Spiral Biotech).

The above-described experiment was performed twice. The results from the two replicates of the experiment are respectively shown in Tables 1 and 2, below. As shown in the results of the first replicate (Table 1), the microbial test system 200 recovered approximately 17-50 more CFU than the Andersen sampler. In the second replicate (Table 2), both the Andersen sampler and the Microbial Test System performed similarly. However, in both instances, the Microbial Test System outperformed the Andersen sampler.

TABLE 1

Replicate #1

| Device | Sampling Time (sec) | Air Volume Sampled (CF) | Average Colony Forming Unit (CFU)/plate | CFU/CF air |
|---|---|---|---|---|
| Andersen | 32 | 0.53 | 1.5 | 2.8 |
| Andersen | 64 | 1.06 | 4.5 | 4.2 |
| Andersen | 128 | 2.13 | 1.5 | 0.7 |
| Andersen | 265 | 4.26 | 5 | 1.1 |
| Microbial Test System | 20 | 0.53 | 74 | 139.6 |
| Microbial Test System | 40 | 1.06 | 74 | 69.8 |
| Microbial Test System | 80 | 2.13 | 105 | 49.3 |
| Microbial Test System | 160 | 4.30 | 75.7 | 17.6 |

TABLE 2

Replicate #2

| Device | Sampling Time (sec) | Air Volume Sampled (CF) | Average CFU/plate | CFU/CF air |
|---|---|---|---|---|
| Andersen | 32 | 0.53 | 3.0 | 5.7 |
| Andersen | 64 | 1.06 | 0.5 | 0.5 |
| Andersen | 128 | 2.13 | 2.0 | 0.9 |
| Andersen | 265 | 4.26 | 4.5 | 1.1 |
| Microbial Test System | 20 | 0.53 | 4.7 | 8.8 |
| Microbial Test System | 40 | 1.06 | 7.3 | 6.9 |
| Microbial Test System | 80 | 2.13 | 15.3 | 7.2 |
| Microbial Test System | 160 | 4.30 | 28.0 | 6.5 |

The results of the above experiments demonstrate that the microbial test system provides comparable or superior microbial detection to the Andersen sampler. The results demonstrate that the levels of impact stress on the microbes (i.e., due to impaction velocity of the microbial cells on the agar surface, design parameters of the microbial test unit, and/or operating parameters) does not negatively affect microbial recovery on the agar.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A compressed gas microbial test unit, comprising:
a housing extending along a longitudinal axis between a first end and a second end, the housing defining an internal cavity comprising a decompression region for decompressing compressed gas input to the internal cavity and a sampling region in fluid communication with the decompression region for containing a growth medium substrate, the decompression region and the sampling region defining a flow path through the internal cavity;
a plate disposed in the internal cavity and separating the decompression region and the sampling region, a surface of the plate defining at least a portion of the decompression region and an edge of the plate defining an outer periphery of the plate, the outer periphery of the plate being radially spaced from an inner surface of the housing with respect to the longitudinal axis;
a gap between the outer periphery of the plate and the inner surface of the housing, the gap defining a passageway for the fluid communication between the decompression region and the sampling region; and
an inlet at the first end of the housing proximate the decompression region and an outlet at the second end of the housing proximate the sampling region, the inlet communicating with the decompression region such that compressed gas entering the decompression region from the inlet is incident on the plate for effectuating decompression of the gas prior to the gas passing through the gap and into the sampling region.

2. The compressed gas microbial test unit of claim 1, wherein the plate is configured to direct the compressed gas incident on the plate radially outward with respect to the longitudinal axis.

3. The compressed gas microbial test unit of claim 1, wherein the internal cavity comprises flow channels proximate the second end extending radially with respect to the longitudinal axis from the outlet.

4. The compressed gas microbial test unit of claim 1, wherein the inner surface of the housing extends along the longitudinal axis and comprises a stepped surface, a first portion of the stepped surface defining at least a portion of the decompression region and a second portion of the stepped surface defining at least a portion of the sampling region.

5. The compressed gas microbial test unit of claim 4, wherein the gap is between the first stepped portion and the edge of the plate and defines the passageway between the decompression region and the sampling region through which the decompressed gas passes from the decompression region into the sampling region.

6. The compressed gas microbial test unit of claim 1, wherein the housing comprises a first portion and a second portion removably attached to the first portion for providing access to the sampling region.

7. A compressed gas microbial test system, comprising:
a housing defining an internal cavity comprising a decompression region for decompressing compressed gas input to the internal cavity and a sampling region in fluid communication with the decompression region, the decompression region and the sampling region defining a flow path through the internal cavity;
a plate disposed in the internal cavity and separating the decompression region and the sampling region, a surface of the plate defining at least a portion of the decompression region and an edge of the plate defining an outer periphery of the plate, the outer periphery of the plate being radially spaced from an inner surface of the housing with respect to the longitudinal axis;
a gap between the outer periphery of the plate and the inner surface of the housing, the gap defining a passageway for the fluid communication between the decompression region and the sampling region;
an inlet at the first end of the housing proximate the decompression region and an outlet at the second end of the housing proximate the sampling region, the inlet communicating with the decompression region such that compressed gas entering the decompression region from the inlet is incident on the plate for effectuating decompression of the gas prior to the gas passing into the sampling region; and
a growth medium substrate contained in the sampling region for collecting microbes present in the gas, the growth medium substrate positioned such that the decompressed gas passing through the gap into the sampling region is incident on the growth medium substrate.

8. The compressed gas microbial test system of claim 7, wherein the plate is configured to direct the compressed gas incident on the plate radially outward with respect to the longitudinal axis.

9. The compressed gas microbial test system of claim 7, wherein the internal cavity comprises flow channels proximate the second end extending radially with respect to the longitudinal axis from the outlet.

10. The compressed gas microbial test system of claim 7, wherein the inner surface of the housing extends along the longitudinal axis and comprises a stepped surface, a first stepped portion of the stepped surface defining at least a portion of the decompression region and a second portion of the stepped surface defining at least a portion of the sampling region.

11. The compressed gas microbial test system of claim 10, wherein the gap is between the first stepped portion and the edge of the plate and defines the passageway between the decompression region and the sampling region through which the decompressed gas passes from the decompression region into the sampling region.

12. The compressed gas microbial test system of claim 7, wherein the housing comprises a first portion and a second portion removably attached to the first portion for providing access to the sampling region.

13. The compressed gas microbial test system of claim 7, further comprising a receptacle disposed in the sampling region and containing the growth medium substrate, the receptacle comprising:
- a base member extending non-parallel to the longitudinal axis that closes off the radially extending channels to form radially extending passages; and
- a side member extending from the base member toward the first end of the housing.

14. The compressed gas microbial test system of claim 13, further comprising a gap between the side member and the housing, the gap between the side member and the housing defining a passageway for effectuating passage of sampled gas into the radially extending passages.

15. The compressed gas microbial test system of claim 7, wherein the growth medium substrate comprises an agar growth medium.

* * * * *